United States Patent [19]

O'Connor et al.

[11] Patent Number: 5,297,962

[45] Date of Patent: Mar. 29, 1994

[54] DENTAL CLEANING DEVICE

[75] Inventors: James D. O'Connor; Cornelius P. O'Connor, both of Hartlepool, England

[73] Assignee: Air-Brush Ltd., Cleveland, England

[21] Appl. No.: 884,438

[22] Filed: May 18, 1992

[30] Foreign Application Priority Data

May 20, 1991 [GB] United Kingdom ................. 9110833
Aug. 30, 1991 [GB] United Kingdom ................. 9118574

[51] Int. Cl.[5] .......................... A61C 5/04; A61G 17/02
[52] U.S. Cl. ........................................... 433/89; 433/80
[58] Field of Search .................. 433/80, 89, 88; 222/3

[56] References Cited

U.S. PATENT DOCUMENTS

| 1,166,033 | 12/1915 | Yoder | 433/89 X |
|---|---|---|---|
| 2,747,775 | 5/1956 | Pritchard . | |
| 4,442,831 | 4/1984 | Trenary | 128/66 |
| 4,787,845 | 11/1988 | Valentine | 433/88 |
| 4,906,187 | 3/1990 | Amadera | 433/80 |
| 4,942,870 | 7/1990 | Damien | 128/66 |
| 4,958,751 | 9/1990 | Curtis et al. | 222/192 |
| 4,993,941 | 2/1991 | Maita et al. | 433/80 |
| 5,082,444 | 1/1992 | Rhoades et al. | 433/80 |
| 5,098,291 | 3/1992 | Curtis et al. | 433/89 |
| 5,127,831 | 7/1992 | Bab | 433/80 |

FOREIGN PATENT DOCUMENTS

| 463545 | 7/1928 | Fed. Rep. of Germany . |
|---|---|---|
| 1641728 | 7/1952 | Fed. Rep. of Germany . |
| 1027945 | 9/1958 | Fed. Rep. of Germany . |
| 1783849 | 12/1958 | Fed. Rep. of Germany . |
| 1932744 | 2/1966 | Fed. Rep. of Germany . |
| 2059428 | 12/1970 | Fed. Rep. of Germany . |
| 2432854 | 1/1976 | Fed. Rep. of Germany . |

Primary Examiner—Gene Mancene
Assistant Examiner—Cindy A. Cherichetti
Attorney, Agent, or Firm—Rodman & Rodman

[57] ABSTRACT

A device for use in removing food debris from between the teeth includes a rigid body having a fluid passage in it extending between a fluid inlet and a fluid outlet, means for connecting the inlet to a source of fluid under pressure, a valve in the passage for controlling fluid flow through the passage, manual means for operating the valve, a rigid tube extending from the fluid outlet to a fluid exit orifice, and pressure relief means between that outlet and the exit orifice.

5 Claims, 3 Drawing Sheets

DENTAL CLEANING DEVICE

The present invention is a device intended for use in removing food debris from between the teeth.

A variety of products is available for cleaning the teeth, including toothbrushes, mouth washes and dental floss, but even the most conscientious use of these products can from time to time leave food debris lodged between the teeth. Toothpicks may usually be used successfully to remove food particles but the use of toothpicks entails a risk of damage to the gums and a consequential risk of infection.

Dentists employ compressed air within a patient's mouth both to remove debris arising from drilling and also to dry a cavity within the tooth before filling it. Thus in theory, compressed gas could be used for dislodging food particles from between the teeth. However the introduction into the mouth of a gas under pressure is a hazardous exercise, since compressed air, inadequately controlled, can penetrate the skin and enter the bloodstream. Thus the simple transfer of this practice from the dentist's surgery to the home, for use by the untrained individual, is neither readily achievable nor safe. However, the use of compressed gas for dental cleaning on a much wider scale is a highly desirable end if a device could be made available which made such use safely practicable by the user himself. It is an object of the present invention to provide such a device.

The dental device according to the invention comprises a rigid body having a fluid passage therethrough extending between a fluid inlet and a fluid outlet, means associated with said fluid inlet for connecting a source of fluid under pressure to said inlet, a valve within said fluid passage for controlling the flow of fluid through said passage, manual means for operating said valve, a rigid elongated tube extending between said fluid outlet and a fluid exit orifice, and pressure relief means between said outlet and said fluid exit orifice.

The device readily lends itself to being constructed in a compact form, suitable for carrying in a handbag or pocket, or in a form suitable for installation in the home, as will be described in more detail below, while retaining the features which make it safe in unskilled hands.

The body of the device may conveniently be generally cylindrical in shape, in which case the fluid passage is preferably disposed along the cylindrical axis for at least a major part of its length. The material of which the body is made should be selected to enable it to withstand safely the pressure of the compressed fluid within it. With this in mind, the body is preferably constructed of metal, for example of carbon steel or stainless steel, or a metal alloy. As one alternative, the body may be made of a rigid polymeric material, optionally reinforced by a metal insert.

A connecting means associated with the fluid inlet enables the passage to be put in communication with a source of fluid under pressure. The most preferred form of the connecting means is a generally cylindrical socket coaxial with the inlet. The socket is preferably threaded internally to enable it to receive directly the outlet nozzle of a compressed fluid cylinder or similar container or alternatively to receive a flexible tube which links the device to a fixed source of compressed fluid at a short distance from the device. Thus the device may be directly attached to a compact gas cylinder and thereby be rendered truly portable. The cylinder may be irremovably secured to the device and be intended to be discarded with the device when the gas is exhausted but it is preferred that the cylinder be detachable to permit it to be replaced by a full cylinder when required. As an alternative, the fluid supply may be a cylinder or other container fixed, for example, to the bathroom wall and linked to the device by a flexible tube. In this way a larger cylinder may be used and will need less frequent replacement.

The release of compressed gas from its source to the exit orifice is controlled by a valve within the fluid passage. The valve member may be one which moves linearly towards and away from the valve seat or it may operate by pivoting relative to the valve seat. A manual means for operating the valve is provided, for example in the form of a lever, a trigger or a push-button. Operation of the valve operating means may simply open the valve and allow gas to be discharged continuously via the exit orifice so long as the means is operated. However, it is preferred that the operation of the valve operating means should release a predetermined quantity of gas from the gas source. For example, activation of the operating means may release gas into a holding chamber within the body of the device, which gas, still under pressure, may be discharged via the exit orifice either when manual pressure is removed from the operating means or when the means is subsequently operated again.

A rigid elongated tube extends from the fluid outlet of the body of the device to the exit orifice and it is this tube which is inserted in the user's mouth. Conveniently, the tube may be angled at a point intermediate its ends. Preferably the tube is tapered somewhat within the region of the exit orifice, in order to reduce its cross-sectional dimension at the orifice and allow more ready manipulation of the orifice end of the tube within the user's mouth. The tube may be formed of any metal or rigid polymeric material which is compatible with insertion into the mouth.

It is an essential and important safety feature of the device according to the invention that pressure relief means be provided between the fluid outlet of the body of the device and the exit orifice. Effective operation of the device requires that the fluid should emerge from the exit orifice at a flow rate sufficiently high to dislodge the food debris but at the same time safety requirements make it essential that, if the exit orifice should become blocked, for example by pressing up against the teeth or gums, then the fluid pressure should be released automatically. The preferred pressure relief means comprises one or more apertures disposed in the cylindrical surface of the rigid tube and communicating directly with the axial bore of the tube. Preferably two or more such apertures are provided. The apertures may advantageously be linked to the tube bore by short radial passages, preferably inclined rearwardly in an outward direction relative to the direction of flow of fluid through the tube.

The invention will now be further described, and further optional features of the invention will become apparent, with reference to the accompanying drawings, which illustrate, by way of example only, five preferred embodiments of the dental device according to the present invention and wherein.

Figure 1:
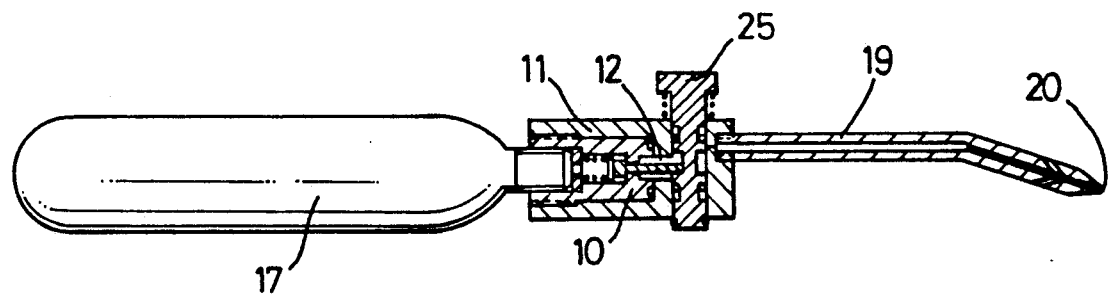
FIG. 1 is a longitudinal sectional view of a first embodiment of the device.
Figure 2:
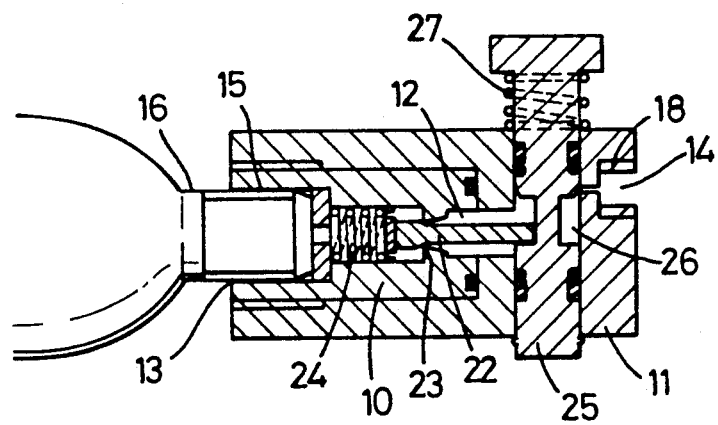
FIG. 2 is a detailed view of the valve of the device of FIG. 1, in a corresponding view and to a larger scale.
Figure 3:
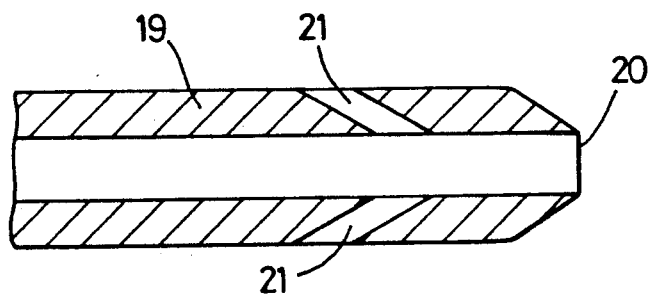
FIG. 3 is a longitudinal sectional view showing, to a larger scale, the exit orifice end of the tube.

The form of the device which is illustrated in FIGS. 1 to 3 comprises a rigid body in the form of two coaxial, generally cylindrical steel parts, namely an inner body part 10 and an outer body part 11. A fluid passage 12 within the body extends between a fluid inlet at 13 and a fluid outlet 14. Coaxially surrounding the inlet 13 is an internally-threaded socket 15 to receive the threaded neck 16 of a cylinder 17 containing compressed air. Coaxially surrounding the fluid outlet 14 is an internally-threaded socket 18 to receive an elongated, angled stainless steel tube 19, which at its distal end tapers to a fluid exit orifice 20. A short distance behind the orifice 20, four short passages 21, inclined rearwardly relative to the orifice and disposed symmetrically around the axis of the tube 19, afford a means of relief of the pressure within the tube if the orifice 20 becomes blocked.

Within the body of the device, a valve member 22 is urged into contact with a corresponding valve seat 23 by a spring 24. The passage 12 within the body tapers towards the valve seat 23 and thus allows the valve member 22 to rock upon the seat 23 and thereby allow compressed air from the cylinder 17 to bleed past the valve.

An operating plunger 25 is disposed diametrically through the body part 11 and intersects the fluid passage 12. An annular channel 26 encircles the plunger 25 and the end of the valve member 22 projects into the channel 26. A return spring 27 urges the plunger 25 upwardly as shown into the position illustrated in FIGS. 1 and 2.

When the illustrated dental device is to be used, the user depresses the plunger 25 against the action of the spring. Downward movement of the plunger first closes off the outlet 14 from the passage 12 and then, by engagement of the channel 26 with the adjacent end of the valve member 22, causes the valve member to pivot upon the valve seat 23 and thereby release air under pressure from the cylinder 17 into the passage 12 and the channel 26. When manual pressure on the plunger 25 is now removed, the compressed air from the passage 12 and channel 26 is able to escape via the outlet 14 and be discharged from the exit orifice 20. By appropriately directing the tube 19, the user is able to direct the discharged jet of air to dislodge debris from between his teeth.

Figure 4:
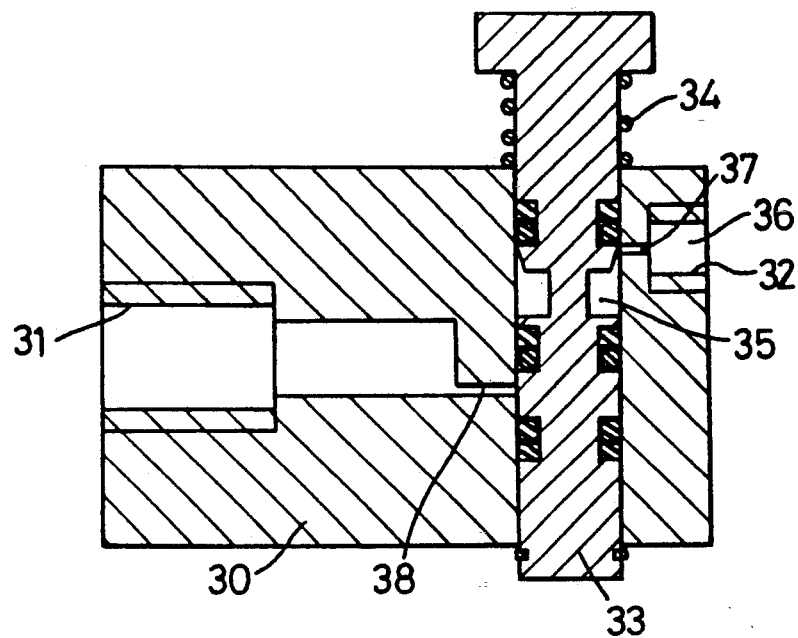
FIGS. 4 to 7 are longitudinal sectional views of four alternative forms of the device, with the rigid elongated tube omitted.

Turning now to FIG. 4, the device illustrated therein is very simply constructed and is of particular benefit in situations where the air pressure does not exceed 1000 psi. The generally cylindrical body 30 of the device is threaded at 31 to receive the threaded neck of a cylinder (not shown) of compressed air and is also threaded at 32 to allow attachment of a stainless steel tube (not shown) such as the tube 19 of FIGS. 1 to 3. A plunger 33 is housed in a bore extending diametrically through the body 30.

The plunger 33 is normally urged into the illustrated position by a compression spring 34, in which position an annular chamber 35, formed between the plunger 33 and its surrounding bore, is in communication with the fluid outlet 36 via a short passage 37. When the plunger is depressed manually against the pressure of the spring 34, the chamber 35 is able to communicate with the compressed air supply via a further short passage 38.

Thus, by pressing the plunger downwardly, the user is able to fill the annular chamber 35 with compressed air, which is subsequently passed via the outlet 36 to the exit orifice of the device when pressure on the plunger is removed.

Figure 5:
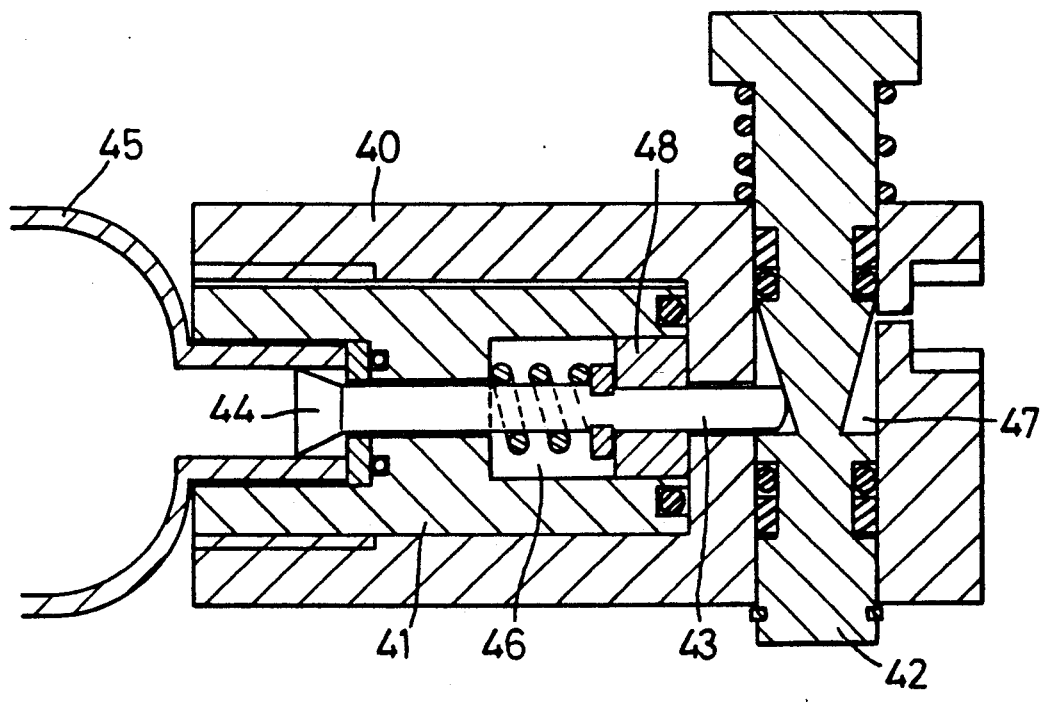

The device shown in FIG. 5 is formed by two coaxial body parts 40 and 41 and includes a manually operated plunger 42 which engages the shaft 43 of a valve 44. When the plunger 42 is depressed, the valve shaft 43 is urged to the left as illustrated and air from the cylinder 45 is able to flow into both a chamber 46 within the body of the device and also a chamber 47 which surrounds the plunger. The total volume of the two chambers, which determines the volume of air eventually discharged, can be modified by the inclusion of a washer 48 in the chamber 46. When the plunger 42 is released, air from the chambers 46 and 47 is discharged at the exit orifice of the device.

Figure 6:
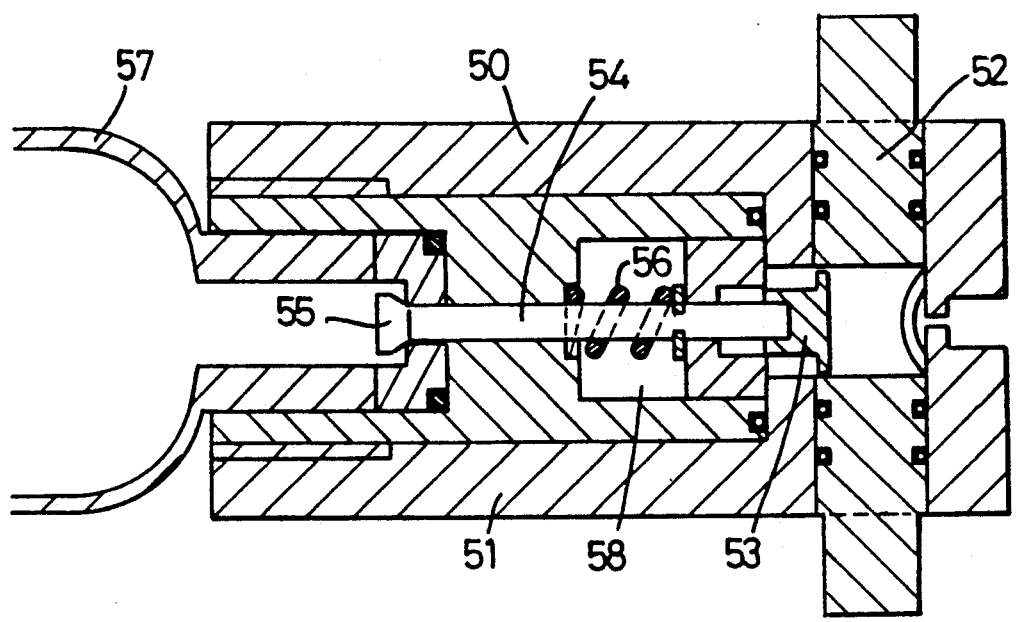
Figure 7:
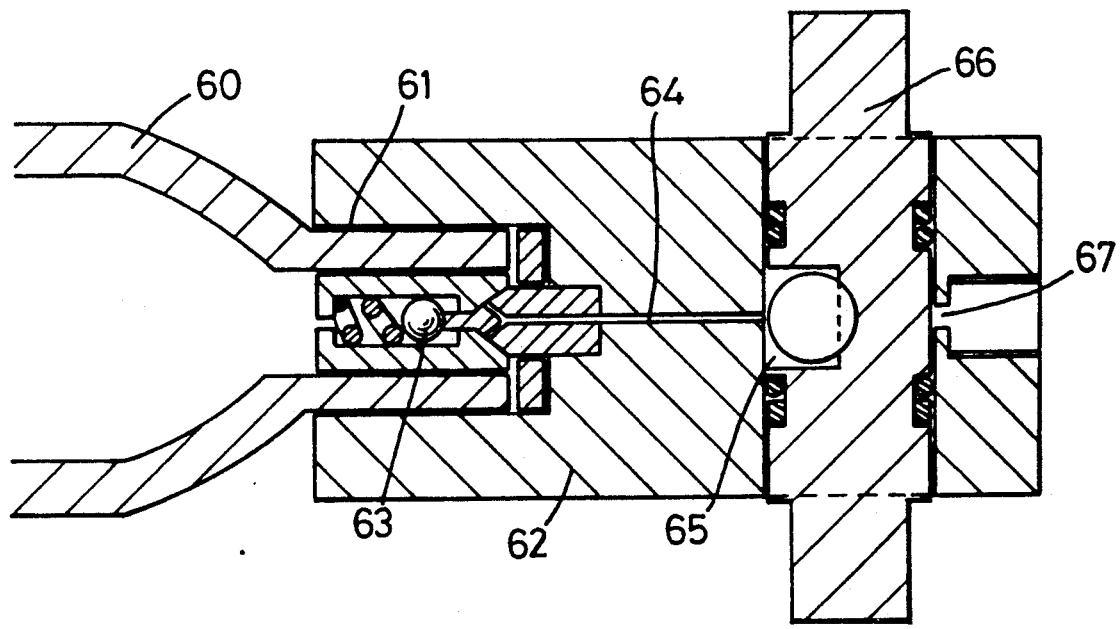

FIGS. 6 and 7 illustrate two forms of the dental device in which the valve includes a rotationally mounted means for operating the valve. The device shown in FIG. 6 again comprises two main body parts, 50 and 51. The operating member 52 is caused to rotate by a manual lever (not shown), whereby it moves from its rest position (illustrated) to a different angular position in which a cam on the member 52 engages a cap 53 on the end of the valve shaft 54 and thereby opens a valve 55 against the pressure of a spring 56. When the valve 55 is opened in this way, compressed air from a cylinder 57 is able to fill a chamber 58 in the body of the device, from which chamber the air is discharged to the exit orifice when the member 52 rotates back to its illustrated position.

Referring finally to the form of the device illustrated in FIG. 7, when the air cylinder 60 is first secured in the socket 61 at the inlet end of the body 62 of the dental device, the valve 63 in the mouth of the cylinder is automatically opened and air under pressure flows via an axial passage 64 into a chamber 65 cut into the operating member 66. Rotation of the member 66 by means of a manual lever (not shown) moves the chamber 65 into a position in which it can discharge the air therein to the exit orifice via a port 67.

While the present invention was devised with the specific aim of providing a dental device, as discussed above, its use is not confined to dental purposes. The device is of value wherever concentrated bursts of compressed air or gas are required. Thus a device of the present type may be carried around by the user with dental purposes in mind but may nonetheless be an invaluable asset in other situations, for example for drying off spark plugs and/or a distributor cap in damp conditions.

We claim:

1. A dental device which comprises a rigid body having a fluid inlet, a fluid outlet and a passage connecting said inlet to said outlet, a valve to control fluid flow from said inlet to said outlet, manual means for operating the valve, a rigid tube extending from the outlet and forming a discharge orifice at its distal end, and pressure relief means between said outlet and said discharge orifice, said operating means being mounted for movement between a first position in which a chamber within said device is placed in communication with said fluid inlet, whereby fluid can flow into said chamber from said inlet, and a second position in which said chamber is placed in communication with said outlet, whereby fluid can flow from said chamber to said outlet.

2. A dental device according to claim 1, wherein said movement of said operating means is a linear movement.

3. A dental device according to claim 1, wherein said movement of said operating means is a rotary movement.

4. A dental device according to claim 1, wherein said pressure relief means comprises at least one passage connecting an axial bore in said rigid tube to an aperture at the surface of said tube.

5. A dental device according to claim 4, wherein said at least one passage is, in an outward direction, inclined towards the end of the rigid tube which is nearer to the fluid outlet.

* * * * *